(12) United States Patent
Lorang et al.

(10) Patent No.: US 12,121,456 B2
(45) Date of Patent: Oct. 22, 2024

(54) GRAFT MATERIAL INJECTOR SYSTEM AND METHOD

(71) Applicant: Spinal Elements, Inc., Carlsbad, CA (US)

(72) Inventors: Douglas M. Lorang, San Jose, CA (US); Jeffrey L Emery, Emerald Hills, CA (US); Andrew Huffmaster, Newark, CA (US); Jarrod W. Taylor, San Gabriel, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 150 days.

(21) Appl. No.: 18/067,225

(22) Filed: Dec. 16, 2022

(65) Prior Publication Data

US 2023/0124332 A1    Apr. 20, 2023

Related U.S. Application Data

(60) Continuation of application No. 16/922,578, filed on Jul. 7, 2020, now Pat. No. 11,564,811, which is a continuation of application No. 16/021,574, filed on Jun. 28, 2018, now Pat. No. 10,709,577, which is a division of application No. 15/018,326, filed on Feb. 8, 2016, now Pat. No. 10,022,243.

(60) Provisional application No. 62/112,969, filed on Feb. 6, 2015.

(51) Int. Cl.
*A61F 2/46*     (2006.01)
*A61B 17/86*    (2006.01)
*A61B 17/88*    (2006.01)

(52) U.S. Cl.
CPC ........ *A61F 2/4601* (2013.01); *A61B 17/8819* (2013.01); *A61B 17/8811* (2013.01); *A61B 17/8825* (2013.01); *A61B 17/8852* (2013.01); *A61F 2002/4627* (2013.01)

(58) Field of Classification Search
CPC .................................................... A61F 2/4601
See application file for complete search history.

(56) References Cited

U.S. PATENT DOCUMENTS

| | | |
|---|---|---|
| 2,002,021 A | 5/1935 | Rouse |
| 3,807,390 A | 4/1974 | Ostrowski et al. |
| 4,846,175 A | 7/1989 | Frimberger |
| 4,862,891 A | 9/1989 | Smith |

(Continued)

FOREIGN PATENT DOCUMENTS

| | | |
|---|---|---|
| DE | 42 22 121 | 9/1993 |
| DE | 197 10 392 | 7/1999 |

(Continued)

OTHER PUBLICATIONS

Official Communication in European Application No. 08730402.8, dated Feb. 18, 2013.

(Continued)

*Primary Examiner* — Christian A Sevilla
(74) *Attorney, Agent, or Firm* — Knobbe, Martens, Olson & Bear, LLP

(57) ABSTRACT

A graft material injector device and method are disclosed. The injector device includes an elongated injector tube and a side loading aperture for receiving graft material. A graft material loader and a cover for the side loading aperture may optionally be included.

19 Claims, 6 Drawing Sheets

(56) References Cited

U.S. PATENT DOCUMENTS

| | | | |
|---|---|---|---|
| 4,863,476 | A | 9/1989 | Shepperd |
| 4,898,161 | A | 2/1990 | Grundei |
| 5,059,193 | A | 10/1991 | Kuslich |
| 5,129,889 | A | 7/1992 | Hahn et al. |
| 5,192,327 | A | 3/1993 | Brantigan |
| 5,201,742 | A | 4/1993 | Hasson |
| 5,219,358 | A | 6/1993 | Bendel et al. |
| 5,267,994 | A | 12/1993 | Gentelia et al. |
| 5,306,310 | A | 4/1994 | Siebels |
| 5,342,394 | A | 8/1994 | Matsuno et al. |
| 5,345,945 | A | 9/1994 | Hodgson et al. |
| 5,366,490 | A | 11/1994 | Edwards et al. |
| 5,374,267 | A | 12/1994 | Siegal |
| 5,383,884 | A | 1/1995 | Summers |
| 5,397,304 | A | 3/1995 | Truckai |
| 5,397,364 | A | 3/1995 | Kozak et al. |
| 5,423,806 | A | 6/1995 | Dale et al. |
| 5,433,739 | A | 7/1995 | Sluijter et al. |
| 5,445,639 | A | 8/1995 | Kuslich et al. |
| 5,470,043 | A | 11/1995 | Marts et al. |
| 5,487,757 | A | 1/1996 | Truckai et al. |
| 5,500,012 | A | 3/1996 | Brucker et al. |
| 5,540,696 | A | 7/1996 | Booth, Jr. et al. |
| 5,549,679 | A | 8/1996 | Kuslich |
| 5,554,163 | A | 9/1996 | Shturman |
| 5,571,147 | A | 11/1996 | Sluijter et al. |
| 5,571,189 | A | 11/1996 | Kuslich |
| 5,599,346 | A | 2/1997 | Edwards et al. |
| 5,697,909 | A | 12/1997 | Eggers et al. |
| 5,716,416 | A | 2/1998 | Lin |
| 5,718,707 | A * | 2/1998 | Mikhail ............... A61F 2/4601 606/93 |
| 5,755,661 | A | 5/1998 | Schwartzman |
| 5,755,732 | A | 5/1998 | Green et al. |
| 5,755,797 | A | 5/1998 | Baumgartner |
| 5,782,832 | A | 7/1998 | Larsen et al. |
| 5,788,713 | A | 8/1998 | Dubach et al. |
| 5,851,214 | A | 12/1998 | Larsen et al. |
| 5,871,501 | A | 2/1999 | Leschinsky et al. |
| 5,885,217 | A | 3/1999 | Gisselberg et al. |
| 5,916,166 | A | 6/1999 | Reiss et al. |
| 5,919,235 | A | 7/1999 | Husson et al. |
| 5,980,471 | A | 11/1999 | Jafari |
| 5,980,504 | A | 11/1999 | Sharkey et al. |
| 6,007,570 | A | 12/1999 | Sharkey et al. |
| 6,019,765 | A * | 2/2000 | Thornhill ............. A61F 2/4601 606/93 |
| 6,039,761 | A | 3/2000 | Li et al. |
| 6,059,829 | A * | 5/2000 | Schlapfer ............. A61F 2/4455 606/247 |
| 6,099,514 | A | 8/2000 | Sharkey et al. |
| 6,126,660 | A | 10/2000 | Dietz |
| 6,126,682 | A | 10/2000 | Sharkey et al. |
| 6,183,517 | B1 | 2/2001 | Suddaby |
| 6,224,630 | B1 | 5/2001 | Bao et al. |
| 6,228,022 | B1 | 5/2001 | Friesem et al. |
| 6,231,609 | B1 | 5/2001 | Mehdizadeh |
| 6,245,072 | B1 * | 6/2001 | Zdeblick ............. A61B 1/3135 623/17.11 |
| 6,245,107 | B1 | 6/2001 | Ferree |
| 6,277,112 | B1 | 8/2001 | Underwood et al. |
| 6,332,895 | B1 | 12/2001 | Suddaby |
| 6,375,635 | B1 | 4/2002 | Moutafis et al. |
| 6,375,682 | B1 | 4/2002 | Fleischmann et al. |
| 6,387,130 | B1 | 5/2002 | Stone et al. |
| 6,409,766 | B1 | 6/2002 | Brett |
| 6,419,704 | B1 | 7/2002 | Ferree |
| 6,436,142 | B1 | 8/2002 | Paes et al. |
| 6,454,806 | B1 | 9/2002 | Cohen et al. |
| 6,468,270 | B1 | 10/2002 | Hovda et al. |
| 6,488,710 | B2 | 12/2002 | Besselink |
| 6,491,690 | B1 | 12/2002 | Goble et al. |
| 6,500,205 | B1 | 12/2002 | Michelson |
| 6,530,926 | B1 | 3/2003 | Davison |
| 6,551,319 | B2 | 4/2003 | Lieberman |
| 6,554,833 | B2 | 4/2003 | Levy et al. |
| 6,558,383 | B2 | 5/2003 | Cunningham et al. |
| 6,558,386 | B1 | 5/2003 | Cragg |
| 6,558,390 | B2 | 5/2003 | Cragg |
| 6,562,033 | B2 | 5/2003 | Shah et al. |
| 6,582,431 | B1 | 6/2003 | Ray |
| 6,592,625 | B2 | 7/2003 | Cauthen |
| 6,595,998 | B2 | 7/2003 | Johnson et al. |
| 6,602,248 | B1 | 8/2003 | Sharps et al. |
| 6,607,505 | B1 | 8/2003 | Thompson et al. |
| 6,607,530 | B1 | 8/2003 | Carl et al. |
| 6,620,196 | B1 | 9/2003 | Trieu |
| 6,656,178 | B1 | 12/2003 | Veldhuizen et al. |
| 6,670,505 | B1 | 12/2003 | Collins et al. |
| 6,676,665 | B2 | 1/2004 | Foley et al. |
| 6,714,822 | B2 | 3/2004 | King et al. |
| 6,726,684 | B1 | 4/2004 | Woloszko et al. |
| 6,733,496 | B2 | 5/2004 | Sharkey et al. |
| 6,749,605 | B2 | 6/2004 | Ashley et al. |
| 6,764,491 | B2 | 7/2004 | Frey et al. |
| 6,767,347 | B2 | 7/2004 | Sharkey et al. |
| 6,773,432 | B1 | 8/2004 | Clayman et al. |
| 6,821,276 | B2 | 11/2004 | Lambrecht et al. |
| 6,830,570 | B1 | 12/2004 | Frey et al. |
| 6,878,155 | B2 | 4/2005 | Sharkey et al. |
| 6,923,811 | B1 | 8/2005 | Carl et al. |
| 6,939,351 | B2 | 9/2005 | Eckman |
| 6,953,458 | B2 | 10/2005 | Loeb |
| 6,964,667 | B2 | 11/2005 | Shaolian et al. |
| 6,976,949 | B2 | 12/2005 | Winkler et al. |
| 7,004,970 | B2 | 2/2006 | Cauthen III et al. |
| 7,008,432 | B2 | 3/2006 | Schlapfer et al. |
| 7,025,765 | B2 | 4/2006 | Balbierz et al. |
| 7,052,516 | B2 | 5/2006 | Cauthen, III et al. |
| 7,056,321 | B2 | 6/2006 | Pagliuca et al. |
| 7,069,087 | B2 | 6/2006 | Sharkey et al. |
| 7,087,055 | B2 | 8/2006 | Lim et al. |
| 7,087,058 | B2 | 8/2006 | Cragg |
| 7,114,501 | B2 | 10/2006 | Johnson et al. |
| 7,124,761 | B2 | 10/2006 | Lambrecht et al. |
| 7,144,397 | B2 | 12/2006 | Lambrecht et al. |
| 7,179,225 | B2 | 2/2007 | Shluzas et al. |
| 7,204,853 | B2 | 4/2007 | Gordon et al. |
| 7,211,055 | B2 | 5/2007 | Diederich et al. |
| 7,241,297 | B2 | 7/2007 | Shaolian et al. |
| 7,252,686 | B2 | 8/2007 | Carrison et al. |
| 7,267,687 | B2 | 9/2007 | McGuckin, Jr. |
| 7,282,020 | B2 | 10/2007 | Kaplan |
| 7,309,336 | B2 | 12/2007 | Ashley et al. |
| 7,318,823 | B2 | 1/2008 | Sharps et al. |
| 7,318,826 | B2 | 1/2008 | Teitelbaum et al. |
| 7,322,962 | B2 | 1/2008 | Forrest |
| 7,331,956 | B2 | 2/2008 | Hovda et al. |
| 7,331,963 | B2 | 2/2008 | Bryan et al. |
| RE40,156 | E | 3/2008 | Sharps et al. |
| 7,618,458 | B2 | 11/2009 | Biedermann et al. |
| 7,682,378 | B2 | 3/2010 | Truckai et al. |
| 7,753,912 | B2 | 7/2010 | Raymond et al. |
| 7,758,647 | B2 | 7/2010 | Arnin et al. |
| 7,771,432 | B2 | 8/2010 | Schwab et al. |
| 7,776,051 | B2 | 8/2010 | Colleran et al. |
| 7,824,445 | B2 | 11/2010 | Biro et al. |
| 7,887,568 | B2 | 2/2011 | Ahlgren |
| 7,901,460 | B2 | 3/2011 | Sherman |
| 7,922,767 | B2 | 4/2011 | Sack et al. |
| 7,947,078 | B2 | 5/2011 | Siegal |
| 7,963,915 | B2 | 6/2011 | Bleich |
| 8,021,429 | B2 | 9/2011 | Viker |
| 8,025,697 | B2 | 9/2011 | McClellan, III et al. |
| 8,083,796 | B1 | 12/2011 | Raiszadeh et al. |
| 8,123,750 | B2 | 2/2012 | Norton et al. |
| 8,128,662 | B2 | 3/2012 | Altarac et al. |
| 8,137,401 | B2 | 3/2012 | Stad et al. |
| 8,142,507 | B2 | 3/2012 | McGuckin, Jr. |
| 8,246,622 | B2 | 8/2012 | Siegal et al. |
| 8,252,001 | B2 | 8/2012 | Quimo et al. |
| 8,252,054 | B2 | 8/2012 | Greenhalgh et al. |
| 8,377,070 | B2 | 2/2013 | Gauthier |
| 8,394,102 | B2 | 3/2013 | Garabedian et al. |

(56) References Cited

U.S. PATENT DOCUMENTS

| | | |
|---|---|---|
| 8,454,617 B2 | 6/2013 | Schaller et al. |
| 8,454,622 B2 | 6/2013 | Blain et al. |
| 8,470,043 B2 | 6/2013 | Schaller et al. |
| 8,579,980 B2 | 11/2013 | DeLurio et al. |
| 8,591,583 B2 | 11/2013 | Schaller et al. |
| 8,628,577 B1 | 1/2014 | Jimenez |
| 8,632,591 B2 | 1/2014 | Vila et al. |
| 8,663,332 B1 | 3/2014 | To et al. |
| 8,685,031 B2 | 4/2014 | Kleiner et al. |
| 8,764,806 B2 | 7/2014 | Abdou |
| 8,906,028 B2 | 12/2014 | Kleiner |
| 8,968,408 B2 | 3/2015 | Schaller et al. |
| 8,974,464 B2 | 3/2015 | Johnson et al. |
| 8,979,860 B2 | 3/2015 | Voellmicke et al. |
| 8,986,385 B2 | 3/2015 | Hall |
| 9,034,041 B2 | 5/2015 | Wolters et al. |
| 9,039,771 B2 | 5/2015 | Glerum et al. |
| 9,161,773 B2 | 10/2015 | Schaller et al. |
| 9,308,022 B2 | 4/2016 | Chitre et al. |
| 9,351,851 B2 | 5/2016 | Huffmaster et al. |
| 9,480,574 B2 | 11/2016 | Lee et al. |
| 9,566,170 B2 | 2/2017 | Schell et al. |
| 9,642,712 B2 | 5/2017 | Schaller et al. |
| 9,827,031 B2 | 11/2017 | Emery et al. |
| 9,955,961 B2 | 5/2018 | Huffmaster et al. |
| 10,022,243 B2 | 7/2018 | Emery et al. |
| 10,231,843 B2 | 3/2019 | Lee et al. |
| 10,258,228 B2 | 4/2019 | Genovese et al. |
| 10,285,821 B2 | 5/2019 | Schaller et al. |
| 10,314,605 B2 | 6/2019 | Huffmaster et al. |
| 10,426,629 B2 | 10/2019 | Schaller et al. |
| 10,575,963 B2 | 3/2020 | Schaller et al. |
| 10,709,577 B2 | 7/2020 | Lorang et al. |
| 10,758,286 B2 | 9/2020 | Ammerman et al. |
| 11,224,453 B2 | 1/2022 | Huffmaster et al. |
| 11,471,145 B2 | 10/2022 | Pacheco-Serrant et al. |
| 2001/0023348 A1 | 9/2001 | Ashley et al. |
| 2001/0029377 A1 | 10/2001 | Aebi et al. |
| 2001/0031981 A1 | 10/2001 | Evans et al. |
| 2002/0019637 A1 | 2/2002 | Frey et al. |
| 2002/0026197 A1 | 2/2002 | Foley et al. |
| 2002/0128716 A1 | 9/2002 | Cohen et al. |
| 2002/0147444 A1 | 10/2002 | Shah et al. |
| 2002/0156530 A1 | 10/2002 | Lambrecht et al. |
| 2003/0009223 A1 | 1/2003 | Fehling et al. |
| 2003/0014047 A1 | 1/2003 | Woloszko et al. |
| 2003/0040796 A1 | 2/2003 | Ferree |
| 2003/0065358 A1 | 4/2003 | Frecker et al. |
| 2003/0083747 A1 | 5/2003 | Winterbottom et al. |
| 2003/0158545 A1 | 8/2003 | Hovda et al. |
| 2003/0158553 A1 | 8/2003 | Michelson |
| 2003/0187453 A1 | 10/2003 | Schlapfer et al. |
| 2003/0204189 A1 | 10/2003 | Cragg |
| 2003/0220650 A1 | 11/2003 | Major et al. |
| 2004/0002762 A1 | 1/2004 | Hawkins |
| 2004/0010315 A1 | 1/2004 | Song |
| 2004/0015218 A1 | 1/2004 | Finch et al. |
| 2004/0024463 A1 | 2/2004 | Thomas, Jr. et al. |
| 2004/0049180 A1 | 3/2004 | Sharps et al. |
| 2004/0059333 A1 | 3/2004 | Carl et al. |
| 2004/0064144 A1 | 4/2004 | Johnson et al. |
| 2004/0073216 A1 | 4/2004 | Lieberman |
| 2004/0087994 A1 | 5/2004 | Suddaby |
| 2004/0092988 A1 | 5/2004 | Shaolian et al. |
| 2004/0102774 A1 | 5/2004 | Trieu |
| 2004/0106940 A1 | 6/2004 | Shaolian et al. |
| 2004/0116922 A1 | 6/2004 | Hovda et al. |
| 2004/0127893 A1 | 7/2004 | Hovda |
| 2004/0133280 A1 | 7/2004 | Trieu |
| 2004/0148028 A1 | 7/2004 | Ferree et al. |
| 2004/0153064 A1 | 8/2004 | Foley et al. |
| 2004/0167625 A1 | 8/2004 | Beyar et al. |
| 2004/0193158 A1 | 9/2004 | Lim et al. |
| 2004/0230198 A1 | 11/2004 | Manzi et al. |
| 2004/0230309 A1 | 11/2004 | DiMauro et al. |
| 2004/0249464 A1 | 12/2004 | Bindseil et al. |
| 2004/0260305 A1 | 12/2004 | Gorensek et al. |
| 2005/0021030 A1 | 1/2005 | Pagliuca et al. |
| 2005/0021041 A1 | 1/2005 | Michelson |
| 2005/0033292 A1 | 2/2005 | Teitelbaum et al. |
| 2005/0038517 A1 | 2/2005 | Carrison et al. |
| 2005/0049623 A1 | 3/2005 | Moore et al. |
| 2005/0065610 A1 | 3/2005 | Pisharodi |
| 2005/0070911 A1 | 3/2005 | Carrison et al. |
| 2005/0080425 A1 | 4/2005 | Bhatnagar et al. |
| 2005/0090833 A1 | 4/2005 | DiPoto |
| 2005/0090899 A1 | 4/2005 | DiPoto |
| 2005/0107878 A1 | 5/2005 | Conchy |
| 2005/0113832 A1 | 5/2005 | Molz, IV et al. |
| 2005/0119750 A1 | 6/2005 | Studer |
| 2005/0131540 A1 | 6/2005 | Trieu |
| 2005/0131541 A1 | 6/2005 | Trieu |
| 2005/0137601 A1 | 6/2005 | Assell et al. |
| 2005/0137605 A1 | 6/2005 | Assell et al. |
| 2005/0149049 A1 | 7/2005 | Assell et al. |
| 2005/0165420 A1 | 7/2005 | Cha |
| 2005/0182414 A1 | 8/2005 | Manzi et al. |
| 2005/0182416 A1 | 8/2005 | Lim et al. |
| 2005/0187537 A1 | 8/2005 | Loeb et al. |
| 2005/0203527 A1 | 9/2005 | Carrison et al. |
| 2005/0222683 A1 | 10/2005 | Berry |
| 2005/0228391 A1 | 10/2005 | Levy et al. |
| 2005/0234493 A1 | 10/2005 | Carr et al. |
| 2005/0240171 A1 | 10/2005 | Forrest |
| 2005/0251134 A1 | 11/2005 | Woloszko et al. |
| 2005/0251177 A1 | 11/2005 | Saadat et al. |
| 2005/0256525 A1 | 11/2005 | Culbert et al. |
| 2005/0261683 A1 | 11/2005 | Veldhuizen et al. |
| 2005/0261684 A1 | 11/2005 | Shaolian et al. |
| 2005/0261692 A1 | 11/2005 | Carrison et al. |
| 2005/0273173 A1 | 12/2005 | Gordon et al. |
| 2005/0278027 A1 | 12/2005 | Hyde |
| 2005/0278036 A1 | 12/2005 | Leonard et al. |
| 2006/0015131 A1 | 1/2006 | Kierce et al. |
| 2006/0025797 A1 | 2/2006 | Lock et al. |
| 2006/0030933 A1 | 2/2006 | DeLegge et al. |
| 2006/0036241 A1 | 2/2006 | Siegal |
| 2006/0041258 A1 | 2/2006 | Galea |
| 2006/0041295 A1 | 2/2006 | Osypka |
| 2006/0047178 A1 | 3/2006 | Winkler et al. |
| 2006/0052793 A1 | 3/2006 | Heinz |
| 2006/0058826 A1 | 3/2006 | Evans et al. |
| 2006/0058876 A1 | 3/2006 | McKinley |
| 2006/0074425 A1 | 4/2006 | Sutterlin et al. |
| 2006/0085070 A1 | 4/2006 | Kim |
| 2006/0089646 A1 | 4/2006 | Bonutti |
| 2006/0116689 A1 | 6/2006 | Albans |
| 2006/0129244 A1 | 6/2006 | Ensign et al. |
| 2006/0136064 A1 | 6/2006 | Sherman |
| 2006/0149268 A1 | 7/2006 | Truckai et al. |
| 2006/0161162 A1 | 7/2006 | Lambrecht et al. |
| 2006/0178666 A1 | 8/2006 | Cosman et al. |
| 2006/0189999 A1 | 8/2006 | Zwirkoski |
| 2006/0195091 A1 | 8/2006 | McGraw et al. |
| 2006/0195094 A1 | 8/2006 | McGraw et al. |
| 2006/0206116 A1 | 9/2006 | Yeung |
| 2006/0217811 A1 | 9/2006 | Lambrecht et al. |
| 2006/0224154 A1 | 10/2006 | Shadduck et al. |
| 2006/0224241 A1 | 10/2006 | Butler et al. |
| 2006/0229625 A1 | 10/2006 | Truckai et al. |
| 2006/0235418 A1 | 10/2006 | Gil et al. |
| 2006/0241577 A1 | 10/2006 | Balbierz et al. |
| 2006/0247600 A1 | 11/2006 | Yeung et al. |
| 2006/0247784 A1 | 11/2006 | Kim |
| 2006/0265076 A1 | 11/2006 | Carter et al. |
| 2006/0265077 A1 | 11/2006 | Zwirkoski |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0010848 A1 | 1/2007 | Leung et al. |
| 2007/0016273 A1 | 1/2007 | Scarborough et al. |
| 2007/0027545 A1 | 2/2007 | Carls et al. |
| 2007/0032791 A1 | 2/2007 | Greenhalgh |

(56) References Cited

U.S. PATENT DOCUMENTS

| | | |
|---|---|---|
| 2007/0050030 A1 | 3/2007 | Kim |
| 2007/0050032 A1 | 3/2007 | Gittings et al. |
| 2007/0055259 A1 | 3/2007 | Norton et al. |
| 2007/0055262 A1 | 3/2007 | Tomita et al. |
| 2007/0060935 A1 | 3/2007 | Schwardt et al. |
| 2007/0067035 A1 | 3/2007 | Falahee |
| 2007/0093822 A1 | 4/2007 | Dutoit et al. |
| 2007/0093899 A1 | 4/2007 | Dutoit et al. |
| 2007/0118219 A1 | 5/2007 | Hyde, Jr. |
| 2007/0123888 A1 | 5/2007 | Bleich et al. |
| 2007/0123903 A1 | 5/2007 | Raymond et al. |
| 2007/0123986 A1 | 5/2007 | Schaller et al. |
| 2007/0149978 A1 | 6/2007 | Shezifi et al. |
| 2007/0149990 A1 | 6/2007 | Palmer et al. |
| 2007/0162032 A1 | 7/2007 | Johnson et al. |
| 2007/0162062 A1 | 7/2007 | Norton et al. |
| 2007/0162127 A1 | 7/2007 | Peterman et al. |
| 2007/0162135 A1 | 7/2007 | Segal et al. |
| 2007/0168041 A1 | 7/2007 | Kadiyala |
| 2007/0168043 A1 | 7/2007 | Ferree |
| 2007/0173939 A1 | 7/2007 | Kim et al. |
| 2007/0175959 A1 | 8/2007 | Shelton, IV et al. |
| 2007/0191837 A1 | 8/2007 | Trieu |
| 2007/0198021 A1 | 8/2007 | Wales |
| 2007/0198025 A1 | 8/2007 | Trieu et al. |
| 2007/0208426 A1 | 9/2007 | Trieu |
| 2007/0213704 A1 | 9/2007 | Truckai et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0225703 A1 | 9/2007 | Schmitz et al. |
| 2007/0233143 A1 | 10/2007 | Josse et al. |
| 2007/0255286 A1 | 11/2007 | Trieu |
| 2007/0255406 A1 | 11/2007 | Trieu |
| 2007/0255703 A1 | 11/2007 | Maruyama et al. |
| 2007/0260252 A1 | 11/2007 | Schmitz et al. |
| 2007/0260270 A1 | 11/2007 | Assell et al. |
| 2007/0260315 A1 | 11/2007 | Foley et al. |
| 2007/0265652 A1 | 11/2007 | Assell et al. |
| 2007/0265691 A1 | 11/2007 | Swanson |
| 2007/0276406 A1 | 11/2007 | Mahoney et al. |
| 2007/0299521 A1 | 12/2007 | Glenn et al. |
| 2008/0009826 A1 | 1/2008 | Miller et al. |
| 2008/0009828 A1 | 1/2008 | Miller et al. |
| 2008/0009847 A1 | 1/2008 | Ricart et al. |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |
| 2008/0015639 A1 | 1/2008 | Bjork et al. |
| 2008/0021435 A1 | 1/2008 | Miller et al. |
| 2008/0027407 A1 | 1/2008 | Miller et al. |
| 2008/0033465 A1 | 2/2008 | Schmitz et al. |
| 2008/0058707 A1 | 3/2008 | Ashley et al. |
| 2008/0065080 A1 | 3/2008 | Assell et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0071356 A1 | 3/2008 | Greenhalgh et al. |
| 2008/0086157 A1 | 4/2008 | Stad et al. |
| 2008/0114367 A1 | 5/2008 | Meyer |
| 2008/0147113 A1 | 6/2008 | Nobis et al. |
| 2008/0161809 A1 | 7/2008 | Schmitz et al. |
| 2008/0177259 A1 | 7/2008 | Wu |
| 2008/0183204 A1 | 7/2008 | Greenhalgh et al. |
| 2008/0221687 A1 | 9/2008 | Viker |
| 2008/0228135 A1 | 9/2008 | Snoderly |
| 2008/0249628 A1 | 10/2008 | Altarac et al. |
| 2008/0287995 A1 | 11/2008 | Gauthier |
| 2008/0294171 A1 | 11/2008 | Boehm, Jr. et al. |
| 2008/0300636 A1 | 12/2008 | Carli et al. |
| 2009/0012612 A1 | 1/2009 | White et al. |
| 2009/0024217 A1 | 1/2009 | Levy et al. |
| 2009/0105711 A1 | 4/2009 | Mitchell et al. |
| 2009/0143716 A1 | 6/2009 | Lowry et al. |
| 2009/0157187 A1 | 6/2009 | Richelsoph |
| 2009/0171390 A1 | 7/2009 | Sankaran |
| 2009/0198241 A1 | 8/2009 | Phan |
| 2009/0198245 A1 | 8/2009 | Phan |
| 2009/0234454 A1 | 9/2009 | Siegal |
| 2010/0030216 A1 | 2/2010 | Arcenio |
| 2010/0114179 A1 | 5/2010 | Moore et al. |
| 2010/0131005 A1 | 5/2010 | Conlon |
| 2010/0179578 A1 | 7/2010 | Tannoury et al. |
| 2010/0185291 A1 | 7/2010 | Jimenez et al. |
| 2010/0198263 A1 | 8/2010 | Siegal et al. |
| 2010/0228091 A1 | 9/2010 | Widenhouse et al. |
| 2010/0249798 A1 | 9/2010 | Sournac et al. |
| 2010/0262147 A1 | 10/2010 | Siegal et al. |
| 2010/0262242 A1 | 10/2010 | Chavatte et al. |
| 2010/0268234 A1 | 10/2010 | Aho et al. |
| 2010/0286782 A1 | 11/2010 | Schaller et al. |
| 2010/0298864 A1 | 11/2010 | Castro |
| 2011/0015638 A1 | 1/2011 | Pischl et al. |
| 2011/0015747 A1 | 1/2011 | McManus et al. |
| 2011/0112455 A1 | 5/2011 | Rocklin |
| 2011/0125266 A1 | 5/2011 | Rodgers et al. |
| 2011/0144440 A1 | 6/2011 | Cropper et al. |
| 2011/0172722 A1 | 7/2011 | Verhulst et al. |
| 2011/0208306 A1 | 8/2011 | Farris |
| 2011/0245926 A1 | 10/2011 | Kitchen |
| 2011/0307063 A1 | 12/2011 | Schaller et al. |
| 2012/0022651 A1 | 1/2012 | Akyuz et al. |
| 2012/0071977 A1 | 3/2012 | Oglaza et al. |
| 2012/0071980 A1 | 3/2012 | Purcell et al. |
| 2012/0089231 A1 | 4/2012 | Prestigiacomo |
| 2012/0123426 A1 | 5/2012 | Quimo |
| 2012/0136442 A1* | 5/2012 | Kleiner ............... A61F 2/4455 |
| | | 623/17.11 |
| 2012/0136448 A1 | 5/2012 | Seifert et al. |
| 2012/0150241 A1 | 6/2012 | Ragab et al. |
| 2012/0232664 A1 | 9/2012 | Ulrich et al. |
| 2012/0277861 A1 | 11/2012 | Steele et al. |
| 2012/0283748 A1 | 11/2012 | Ortiz et al. |
| 2012/0296171 A1 | 11/2012 | Lovell et al. |
| 2013/0053863 A1 | 2/2013 | Juravic et al. |
| 2013/0110239 A1 | 5/2013 | Siegal et al. |
| 2013/0116791 A1 | 5/2013 | Theofilos |
| 2013/0144391 A1 | 6/2013 | Siegal et al. |
| 2013/0158667 A1 | 6/2013 | Tabor et al. |
| 2013/0204374 A1 | 8/2013 | Milella, Jr. |
| 2013/0238098 A1 | 9/2013 | Schaller et al. |
| 2013/0282143 A1 | 10/2013 | Perkins et al. |
| 2013/0304070 A1 | 11/2013 | Nelson et al. |
| 2014/0058513 A1 | 2/2014 | Gahman et al. |
| 2014/0067073 A1 | 3/2014 | Hauck |
| 2014/0163326 A1 | 6/2014 | Forsell |
| 2014/0163560 A1 | 6/2014 | Fenn et al. |
| 2014/0235949 A1 | 8/2014 | Smith |
| 2014/0236296 A1 | 8/2014 | Wagner et al. |
| 2014/0249629 A1 | 9/2014 | Moskowitz et al. |
| 2014/0257484 A1 | 9/2014 | Flower et al. |
| 2014/0277481 A1 | 9/2014 | Lee et al. |
| 2014/0316427 A1 | 10/2014 | Yoon et al. |
| 2015/0012000 A1 | 1/2015 | Siegal et al. |
| 2015/0051701 A1 | 2/2015 | Glerum et al. |
| 2015/0100124 A1 | 4/2015 | Whipple |
| 2015/0112437 A1 | 4/2015 | Davis et al. |
| 2015/0112438 A1 | 4/2015 | McLean |
| 2015/0148908 A1 | 5/2015 | Marino et al. |
| 2015/0367487 A1 | 12/2015 | Nino et al. |
| 2016/0007979 A1 | 1/2016 | Bhagat et al. |
| 2016/0287409 A1 | 10/2016 | Ziemek |
| 2016/0367332 A1 | 12/2016 | Shah et al. |
| 2017/0135704 A1 | 5/2017 | Abbasi |
| 2017/0303938 A1 | 10/2017 | Rindal et al. |
| 2019/0167440 A1 | 6/2019 | Lee et al. |
| 2019/0216482 A1 | 7/2019 | Huffmaster et al. |
| 2019/0216612 A1 | 7/2019 | Schaller et al. |
| 2020/0345401 A1 | 11/2020 | McHale et al. |
| 2021/0113252 A1 | 4/2021 | Ammerman et al. |
| 2021/0154024 A1 | 5/2021 | Lorang et al. |
| 2021/0169459 A1 | 6/2021 | Pacheco-Serrant et al. |

(56) References Cited

U.S. PATENT DOCUMENTS

| | | | |
|---|---|---|---|
| 2022/0031471 | A1 | 2/2022 | Hessler et al. |
| 2022/0110650 | A1 | 4/2022 | Huffmaster et al. |

FOREIGN PATENT DOCUMENTS

| | | |
|---|---|---|
| EP | 0 682 910 | 11/1995 |
| EP | 1 157 676 | 11/2001 |
| FR | 2 900 814 | 11/2007 |
| JP | 2002-028171 | 1/2002 |
| WO | WO 95/025485 | 9/1995 |
| WO | WO 98/017190 | 4/1998 |
| WO | WO 98/034552 | 8/1998 |
| WO | WO 99/021500 | 5/1999 |
| WO | WO 99/047058 | 9/1999 |
| WO | WO 00/074605 | 12/2000 |
| WO | WO 01/001895 | 1/2001 |
| WO | WO 03/024344 | 3/2003 |
| WO | WO 2005/048856 | 6/2005 |
| WO | WO 2006/042334 | 4/2006 |
| WO | WO 2006/047587 | 5/2006 |
| WO | WO 2006/072941 | 7/2006 |
| WO | WO 2007/009107 | 1/2007 |
| WO | WO 2007/079237 | 7/2007 |
| WO | WO 2007/100914 | 9/2007 |
| WO | WO 2008/021972 | 2/2008 |
| WO | WO 2008/036505 | 3/2008 |
| WO | WO 2008/063435 | 5/2008 |
| WO | WO 2008/084479 | 7/2008 |
| WO | WO 2008/103832 | 8/2008 |
| WO | WO 2008/112308 | 9/2008 |
| WO | WO 2010/008353 | 1/2010 |
| WO | WO 2011/150350 | 12/2011 |
| WO | WO 2012/048187 | 4/2012 |
| WO | WO 2012/178018 | 12/2012 |
| WO | WO 2013/043850 | 3/2013 |
| WO | WO 2014/158680 | 10/2014 |
| WO | WO 2019/148083 | 8/2019 |
| WO | WO 2019/178575 | 9/2019 |

OTHER PUBLICATIONS

International Search Report and Written Opinion in International Application No. PCT/US2008/054590, dated Aug. 22, 2008.
International Preliminary Report on Patentability and Written Opinion in International Application No. PCT/US2008/054590, dated Aug. 28, 2009.
International Search Report and Written Opinion in International Application No. PCT/US2019/015386, dated May 23, 2019.
International Preliminary Report on Patentability and Written Opinion in International Application No. PCT/US2019/015386, dated Aug. 13, 2020.
International Search Report and Written Opinion in International Application No. PCT/US2019/022632, dated May 30, 2019.
International Preliminary Report on Patentability and Written Opinion in International Application No. PCT/US2019/022632, dated Oct. 1, 2020.
International Search Report and Written Opinion in International Application No. PCT/US2014/019246, dated Aug. 19, 2014.
International Preliminary Report on Patentability and Written Opinion in International Application No. PCT/US2014/019246, dated Sep. 24, 2015.
Office Communication for U.S. Appl. No. 13/804,847, dated Jul. 13, 2015.
Office Communication for U.S. Appl. No. 13/804,847, dated Oct. 16, 2015.
Extended European Search Report for European Patent Application No. 11787510.4, dated Oct. 15, 2013.
International Search Report and Written Opinion for PCT Patent Application No. PCT/US2011/038377, dated Aug. 25, 2011.
International Search Report and Written Opinion for PCT Patent Application No. PCT/US2013/068906, dated Feb. 6, 2014.

\* cited by examiner

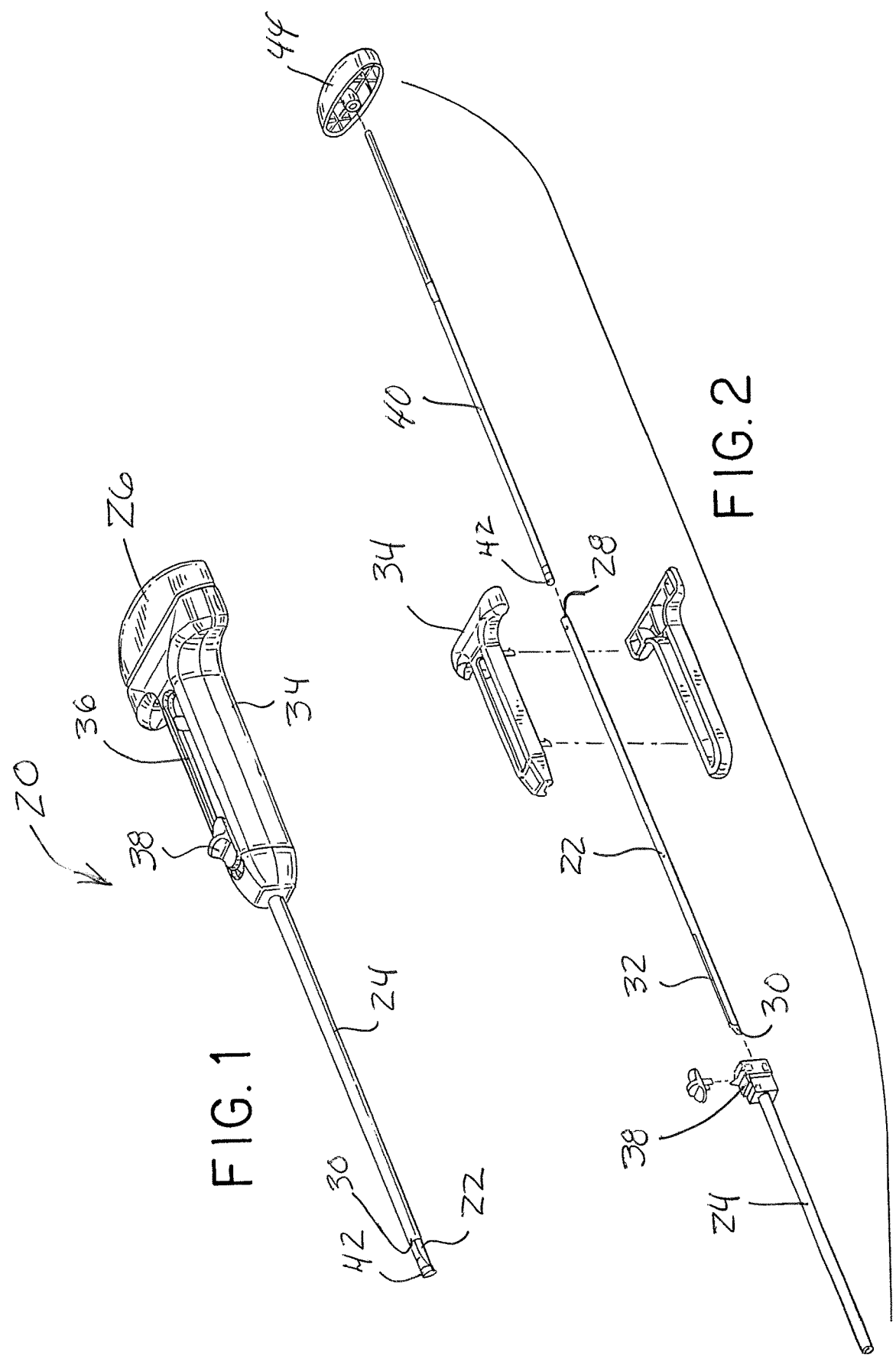

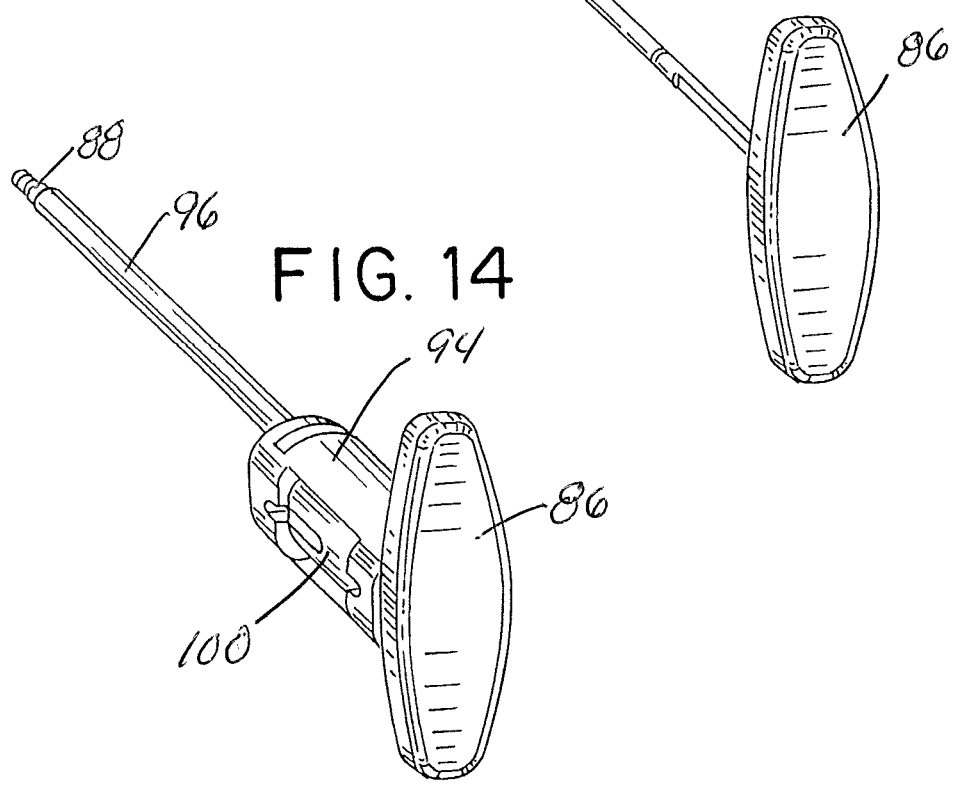

GRAFT MATERIAL INJECTOR SYSTEM AND METHOD

This application is a continuation of U.S. patent application Ser. No. 16/922,578, filed Jul. 7, 2020, which is a continuation of U.S. patent application Ser. No. 16/021,574, filed Jun. 28, 2018, now U.S. Pat. No. 10,709,577, which is a division of U.S. Patent Application No. 15/018,326, filed on Feb. 8, 2016, now U.S. Pat. No. 10,022,243, which claims priority to and the benefit of U.S. Provisional Application No. 62/112,969, filed Feb. 6, 2015, all of which are hereby incorporated herein by reference.

FIELD OF THE DISCLOSURE

The present invention pertains to devices for minimally invasive procedures in the field of orthopedic surgery and more particularly to deployment of bone graft material into the disc space during a fusion procedure.

BACKGROUND

A major cause of chronic, and often disabling, back pain is disruption or degeneration of an intervertebral disc. The spine is comprised of bony vertebrae separated by intervertebral discs. Each intervertebral disc connects adjacent vertebrae and forms a form of joint that allows movement of the vertebral column. An intervertebral disc is generally divided into two regions: the nucleus pulposus and the annulus fibrosus. The nucleus pulposus is a gelatinous-like tissue that lies at the center of the disc and provides a cushion between adjacent vertebrae. The annulus is made up of collagen fibers that form concentric lamellae that surround and contain the nucleus pulposus.

There are many causes of disruption and degeneration of intervertebral discs, which can be broadly categorized as mechanical, genetic and biochemical. Mechanical damage includes herniation in which a portion of the nucleus pulposus projects through a fissure or tear in the annulus fibrosus. Genetic and biochemical causes usually result from changes in the biochemical processes of a disc. Such changes can be attributed to genetic disorders or environmental influences. Degenerative disc condition is commonly caused by a change in the biochemical process of an intervertebral disc. Such degeneration is a progressive process that usually begins with a decrease in the ability of the nucleus pulposus to absorb water. With a loss of water content, the nucleus becomes dehydrated, resulting in a decrease of internal disc hydraulic pressure, and ultimately to a loss of disc height. This loss of disc height can cause the annulus to buckle, eventually resulting in annular fissures and ruptures. Herniation occurs when a rupture leads to protrusion of the nucleus pulposus through the annulus.

Furthermore, disc height plays an important role in the functionality of the intervertebral disc and spinal column, and changes in disc height can have both local and wider effects. On the local (or cellular) level, decreased disc height may result in increased pressure in the nucleus pulposus, which can lead to a decrease in normal cell operation and an increase in cell death and disintegration. In addition, increases in intra-discal pressure may create an unfavorable environment for fluid transfer into the disc, which can cause a further decrease in disc height.

Decreased disc height also results in significant changes in the larger mechanical stability of the spine. With decreasing height of the disc, the facet joints bear increasing loads and may undergo hypertrophy and degeneration. Decreased stiffness of the spinal column and increased range of motion resulting from loss of disc height can lead to further instability of the spine, as well as back pain.

Several disc defects may be treated by implantation of a prosthetic into the nuclear space of the intervertebral disc. Some procedures that may include insertion of a prosthetic into the disc are spinal fusion and disc repair and replacement. Prior to implantation of most prostheses, a discectomy is often performed to prepare the nuclear space for implantation of the prosthetic and, when spinal fusion is desired, to facilitate bony fusion between the vertebral bodies. Some implantation procedures may require a total discectomy in which the majority (and usually all) of the volume of the nucleus pulposus is removed. Others may require a partial discectomy in which only a portion of the nucleus pulposus is removed.

Traditionally, when a fusion is the desired treatment option, there are several approaches to access the disc space and position an implant to regain the proper disc height. For a typical posterior surgical approach, an incision is made through the back of a patient and access to the disc space is achieved. Manual instruments are used and inserted through the access to the intervertebral disc requiring treatment. The curettes and rongeurs are used to cut, tear, and remove nucleus pulposus tissue one piece at a time, and the rasps are utilized to roughen or scrape the endplates of adjacent vertebrae. Other options have been disclosed previously to provide a more accurate and minimally invasive disectomy such as disclosure "Disc preparation tools and methods using the same" U.S. Application Ser. No. 62/021,960, filed Jul. 8, 2014.

Once the disc has been removed, the implantation of the intervertebral implant device can be achieved. Such devices and methods have also been previously disclosed in application "Device for treating the Spine" U.S. application Ser. No. 12/035,298, filed Feb. 21, 2008, and more particularly, in application "Spinal fusion implants and devices and methods for deploying such implants" U.S. application Ser. No. 13/803,322, filed Mar. 14, 2013 and incorporated by reference herein.

A further component needed in the fusion process to create bony fusion between the two vertebral bodies and that is bone graft material or bone filler material (both of which are generally referred to herein as graft material). Such material will favor the creation of a bony bridge that spans across the implant and connects the inferior (lower) cartilaginous endplate of the superior (upper) vertebral body to the superior (upper) cartilaginous endplate of the inferior (lower) vertebral body.

Traditionally, the graft material (bone graft material and/or bone filler material) is positioned into the implant, such as a cage, prior to insertion into the disc space and due to this process cannot be fully optimized for best endplate to endplate contact.

In addition, previous graft delivery systems are backloading, such that the graft material must be advanced a great distance through the barrel before it is extruded into the delivery site. More work (force applied over a greater distance) is therefore required to achieve this successfully, and often the nature of the graft material may cause significant binding when pushed over longer distances, rendering the device unusuable.

Minimally invasive spinal surgery requires that all surgical tools be as small as possible to minimize tissue trauma and exposure to the surgical site. Tools to deliver bone graft that have a delivery diameter of 10 mm or less are highly susceptible to requiring large forces to deliver the bone graft material or, in the worst case, may seize entirely because of the high resistance developed when pushing materials of large, irregular grain size like autograft bone graft material. This susceptibility to seizing is aggravated by the length over which the graft must be delivered down the tool, which is typically 6 or more inches if the material is loaded at the most proximal tube position and pushed all the way to the delivery site.

Typical bone graft tools incorporate a proximal funnel, a long tube length, and a manual tamp that requires the user to tap to deliver the graft to the site. Large bone chips loaded into the tube chamber can contribute significantly to delivery resistance. To overcome the resistance, the outer diameter of the delivery tube is often quite large (>10 mm). Further, the loading of these long-bored funnels must be done at the surgical site, lest the material fall out at an undesirable location. Thus, this requires the primary surgeon to load and tamp the graft material into place.

There continues to be a need for further development and advancement in this field. For instance, in disclosure PCT publication WO 2014/158680 (incorporated by reference herein) FIG. 32 shows a cannula that extends thru the side wall of an implant device to introduce the bone graft material but no specific device or method is disclosed.

SUMMARY

In accordance with one aspect of the present subject matter, a bone graft material injector is provided comprising: an injector device including an elongated injector tube, an internal injector tube lumen extending through the injector tube and having a longitudinal axis, a distal injection aperture communicating with the lumen and a side loading aperture for receiving a quantity of graft material into axial alignment with the lumen axis; and a graft material loader cooperatively engageable with the side loading aperture and adapted to load a selected quantity of graft material into axial alignment with the axis of the injector tube lumen.

In another aspect a graft material injector device is provided comprising: an elongated injector tube including an internal lumen; a distal injection aperture communicating with the injector tube internal lumen and a side loading aperture communicating with the lumen; and a cover associated with the side loading aperture and movable between a position substantially closing the side loading aperture and a position substantially opening the side loading aperture for loading graft material into the internal lumen.

In a further aspect, as a graft material injector is provided comprising: elongated injector assembly comprising an inner elongated injector tube and outer elongated cannula tube, the injector tube including a proximal end portion and a distal end portion with a lumen extending therethrough; a handle secured to the proximal end portion of the injector tube; an injection aperture in the distal end portion of the injector tube; and an elongated side loading aperture in the injector tube proximal of the injection aperture. The outer cannula is sized to movably receive the injector tube therein, and the cannula and tube are relatively movable between a position in which the cannula substantially covers the side loading aperture to close the side loading aperture and a position in which the cannula does not substantially cover the side loading aperture to open the side-loading aperture for receiving graft material into the injector tube lumen. The handle includes an actuator engaged with the cannula for sliding the cannula between the positions substantially covering the side loading aperture and not substantially covering the side loading aperture.

In accordance with another aspect, a method is provided for injecting graft material into a spine disc surgery site employing any of the above apparatus. More specifically, a method of injecting graft material into cooperative association with a spine disc implant is provided comprising: introducing graft material into axial alignment with an injector tube lumen through a side loading aperture; closing the side loading aperture; positioning the distal end of the tube into the desired position with respect to the implant; and moving a push rod through the lumen, thereby applying force to the graft material to force it out the injection aperture and into association with the implant.

These and other aspects are found in the drawings hereof and the detailed description below.

DETAILED DESCRIPTION OF DRAWINGS

FIG. 1 is a perspective view that shows one embodiment of a graft material injector device.

FIG. 2 shows an exploded perspective view of graft injector device of FIG. 1.

FIG. 13 is a perspective view of the graft material injector device of FIG. 12, with components in different operative positions.

FIG. 14 is a perspective view of the graft material injection device of FIG. 11 taken from a different angle.

DETAILED DESCRIPTION

Figure 3:
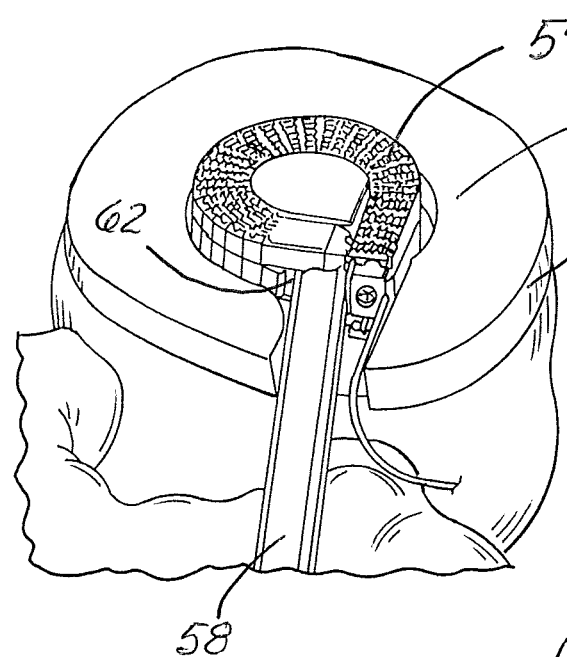
FIG. 3 shows one embodiment of a possible application for the bone graft injector of FIG. 1.

FIGS. 1 and 2 depict one non-limiting example of a fusion graft material injection assembly or device generally at 20 embodying certain aspects of the present subject matter. The illustrated injection device 20 includes an elongated injector tube 22, that is axially relatively movable with respect to an outer cannula 24, and a pusher 26 that is advancable through the injector tube. The elongated injector tube has an internal lumen extending between a proximal end opening 28 and a distal end opening 30. A side loading aperture illustrated in the form of an elongated slot 32 in the wall of the injector tube, is located preferably but not exclusively in the distal end portion of the tube proximal of the distal end opening 26. The distal tip of the injector tube could be square cut or beveled to facilitate entry into tighter locations. A beveled tip could be oriented with respect to injector tube handle 34 to be indicative to the surgeon of bevel opening direction. The tip could also have longitudinally oriented slits that could allow the tube to collapse into tighter spaces and then expand when graft material and pusher 26 are advanced through the injector tube lumen. Alternatively, the tip of the injector tube could be made of soft, pliable, non-atraumatic material. The injector tube, cannula and/or pusher may be made of any suitable material, such as stainless steel or rigid plastic.

Handle 34 is attached to the proximal end portion of the injector tube 22 and is ergonomically configured for gripping ease. The handle includes a proximal opening in axial alignment with the injector tube lumen to receive the pusher 26. The illustrated handle includes an axially extending slot 36 that slidably receives an actuator, such as a thumb tab 38, connected to the proximal end of cannula 24. Pusher 26 includes an elongated rod or pin 40 having a closed distal end 42. An ergonomically shaped handle 44 is secured to a proximal end of the rod.

The cannula 24 and injector tube 22 are respectively sized for close fitting but still slidable engagement between the outer surface of the injector tube and the inner lumen surface of the cannula. With this arrangement, the cannula 24 defines, in effect, a cover that is movable relative to the injector tube between (1) a substantially open or uncovered position that exposes the side aperture or elongated slot 32 for loading graft material into the injector tube, and (2) a substantially closed or covered position, where the cannula extends over and covers the slot 32 after graft material has been introduced into the slot.

Similarly, the injector tube lumen and the pusher rod 40 are respectively sized for close fitting but relatively movable engagement. As explained herein, the pusher is used to push against graft material that has been loaded into the injector tube so as to apply force against the graft material and push it out the distal end opening 30 of the injector tube. The relative close fit between the pusher rod 40 and injector tube lumen prevents substantial amounts of graft material from entering the spacing between the pusher rod distal end and the injector tube lumen when the pusher rod is advanced against graft material in the injector tube lumen. The illustrated pusher 26 is configured for slidable moving of the pusher rod 40 within the injector tube lumen. However, the injector device may also be configured with a threaded engagement between the pusher 26 and injector tube or injector tube handle such that rotation of the pusher handle 44, which could be in the form of a knob, advances the pusher rod within and along the injector tube lumen. Threaded engagement may provide greater control of injection rate and/or volume and provide mechanical advantage over a sliding arrangement. As a further alternative, the pusher rod 40 could be significantly smaller than the injector tube lumen, but terminate at a larger distal end such as a flexible, compliant polymeric or low-friction tip that is closely sized relative to the injector tube lumen or in a state of compression therein so as to fully fill the lumen. Still another alternative is for the plunger distal tip to be of metal to provide a stiff rigid member that can be used as a graft material tamp after the material is ejected from the distal end of the injector tube.

While FIGS. 1 and 2 show a graft injection device or assembly 20 with an injector tube 22 having side loading aperture in the form of a single elongated slot 32, the injector tube may have more than one loading aperture, and the aperture(s) may be of any suitable size or shape. Because bone graft material can include bone chips or particles of relatively large size that clog or impede delivery through the injector tube, the side loading aperture may also include or be in the form of a filter mesh or sieve that allows only graft material below a certain size to pass into the injector tube lumen. Such a filter or sieve may take any suitable configuration and may be in the form of pores or slits laser cut through the side wall of the injector tube.

Figure 4:
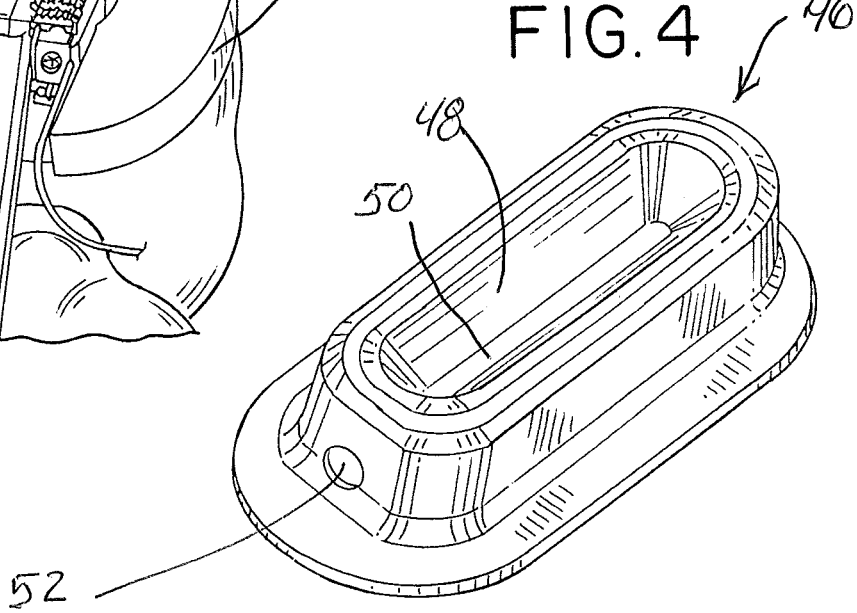
FIG. 4 is a perspective view that shows one embodiment of a potential loading hopper or graft material guide.

In the illustrated embodiment, the graft material device assembly may optionally include a guide or hopper 46 to assist in introducing graft material into the injector tube. The guide may have any suitable shape. As illustrated in FIG. 4, the guide is in the form of a funnel having a funnel wall 48 inclined toward a funnel outlet 50. More particularly, in this non-exclusive embodiment the guide is elongated and has an elongated outlet substantially the same length at the elongated slot 32 in the injector tube 22. The width of the outlet slot 50 in the guide may be approximately the width of the elongated slot 32 or may have a wider or narrower width. A narrower width may be selected to prevent graft particles exceeding a certain size from entering the injector tube. In this form, the elongated funnel outlet acts as a filter or sieve. Alternatively, a separate filter or sieve structure may be located in the funnel outlet or otherwise mounted in the funnel to filter or sieve the graft material. The size and profile of the guide affords a stable, horizontal loading position for introducing graft material into the injector tube. Variations of these features allow the guide and injector device to be adapted to change the angle of orientation with respect to the user, such as a 30° or 45° angle.

The illustrated guide 40 includes an injector tube guide in the form of an opening or aperture 52 into which the injector tube is inserted for graft material loading purposes. The opening 52 is located so as to cause alignment of the elongated slot 32 in the injector tube 22 with the elongated outlet 50 in the funnel-shaped guide 46 when the injector tube is inserted into the aperture 52. More specifically, when the injector tube is inserted into the aperture 52 of the funnel, the elongated slot 32 and elongated outlet 50 are in registration and contact so that graft material can be forced, typically by manually applied pressure, from the funnel into the injector tube. This provides a selected quantity or bolus of graft material in the injector tube having a length approximately that of the elongated slot 32 and a diameter or cross-sectional size of the injector tube lumen.

Figure 5:
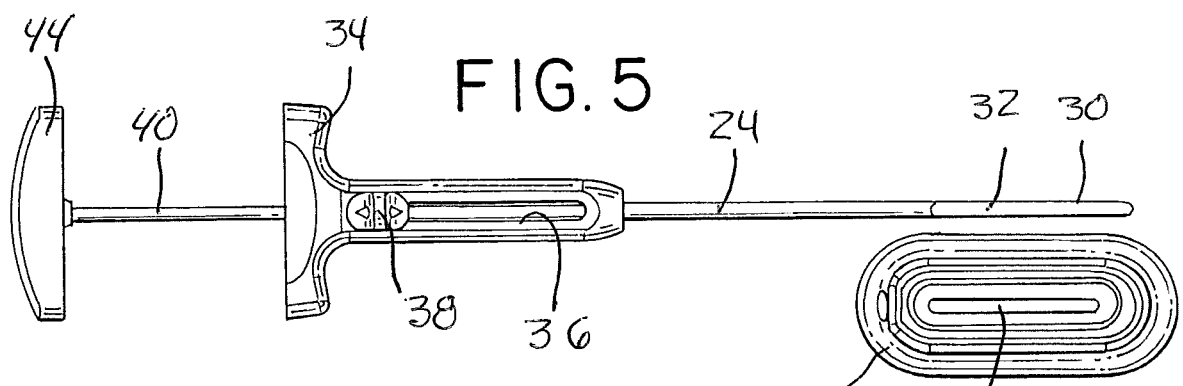
FIG. 5 shows one embodiment of a potential step one of the usage of the device.

Steps for introducing graft material into the injector tube are generally illustrated in FIGS. 5-9. FIG. 5 shows the graft injection assembly in a loading configuration with the pusher 26 withdrawn to a position where the distal end of pusher rod 40 is proximal of the elongated slot 32. Similarly, the thumb tab 38 of the cannula 24 is slid to the proximal end of handle slot 36. In this position, the cannula 24 is retracted to substantially and preferably completely uncover the elongated slot 32 of the injection tube 22.

Figure 6:
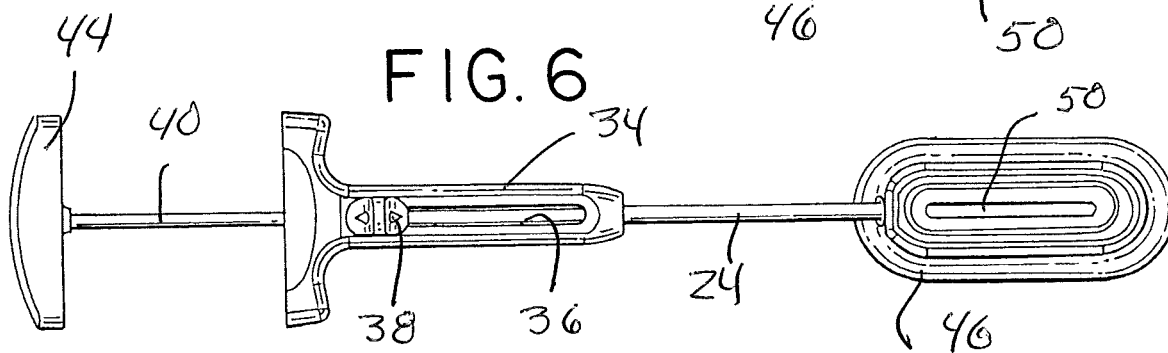
FIG. 6 shows one embodiment of a potential step two of the usage of the device.

FIG. 6 depicts the injector assembly, in the loading configuration of FIG. 5, with the injector tube inserted into opening 52 of guide 46. This positions the elongated slot of the injector tube in registration with the elongated outlet 50 of the funnel shaped guide. (FIG. 7 is essentially similar to FIG. 6.)

Figure 7:
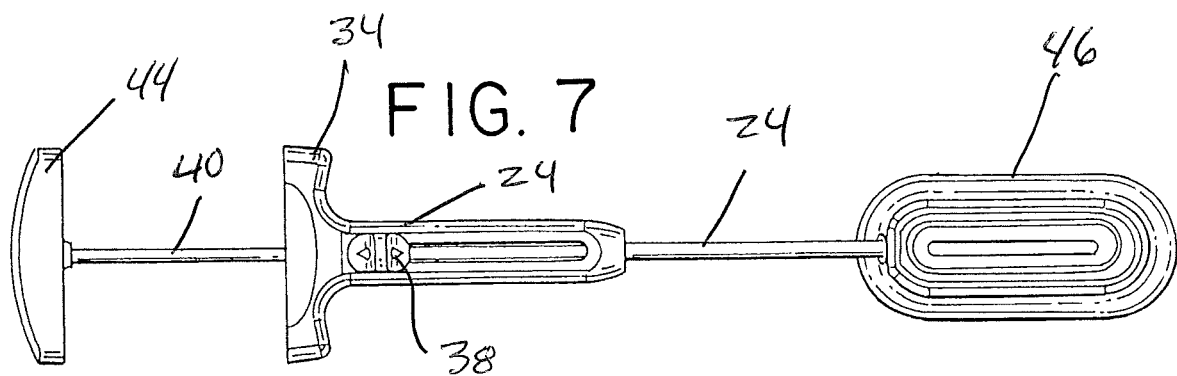
FIG. 7 shows one embodiment of a potential step two of the usage of the device.

In the position of FIGS. 6 and 7, graft material may be forced, by manual pressure or tamp, from the funnel shaped guide, through the elongated outlet 50 and elongated injector tube slot 32, into the injector tube lumen, filling it with a selected amount (e.g., about 1 cc) of graft material axially positioned within the lumen.

Figure 8:
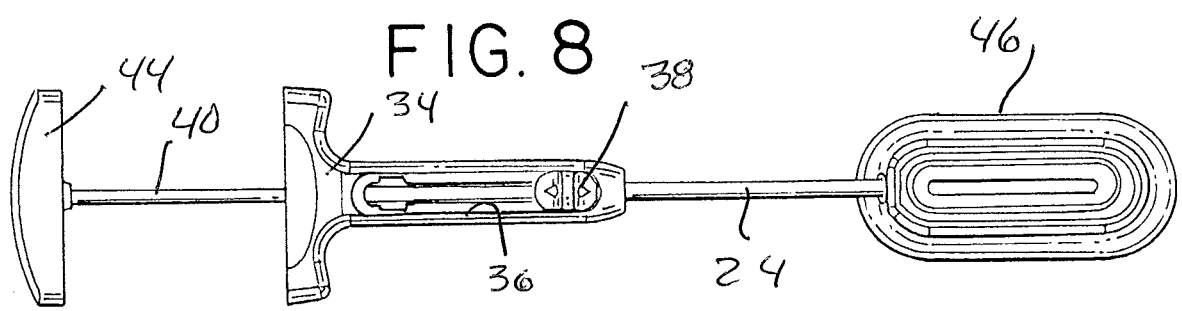
FIG. 8 shows one embodiment of a potential step three of the usage of the device.
Figure 9:
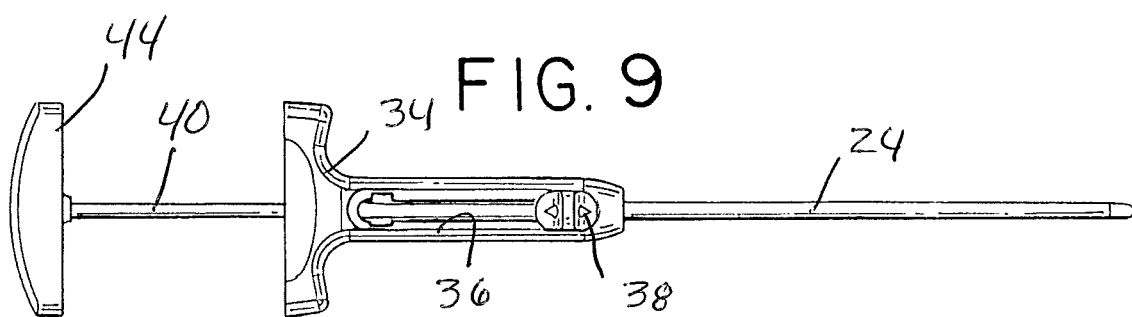
FIG. 9 shows one embodiment of a potential step four of the usage of the device.
Figure 10:
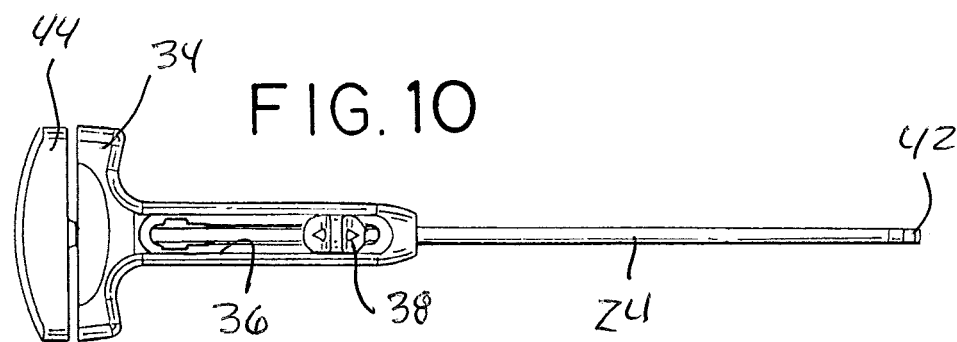
FIG. 10 shows one embodiment of a potential step five of the usage of the device.

The cannula 24 is then moved to the distal position in the handle slot 36, as shown in FIG. 8. This covers and closes the slot, readying the assembly for the next steps. The injector assembly is then withdrawn from the guide 46, with the pusher 26 still in the retracted position, as seen in FIG. 9.

The distal end portion injection assembly is then introduced into the surgical site where the graft material is required. One such surgical site may be the intradiscal space of the human spine. FIG. 3 shows such an exemplary site, with an implant 54 located within a central area of a disc 56, from which the nucleus has been removed in preparation for the procedure. An access tube 58 is shown extending through an access opening in the disc annulus 60 and into a window 62 in the disc implant. The distal end of the injector tube 22 and cannula 24 may be inserted through the access tube or directly into the implant window (without an access tube), requiring only a small access opening in the tissue, such as about 5 mm, that reduces risk of tissue trauma. When suitably located, the pusher 26 is advanced while the injector tube is held fixed. The distal end of the pusher rod 40 engages and pushes the length of graft material along the distal end portion of the injector tube and out the distal end opening 30 into the central space within the implant. The travel of the pusher rod may be configured to optimize or indicate to the user the volume of graft material dispensed or the maximum volume dispensed. Of course, the illustrated implant is but one example, and the fusion graft injection assembly or device as described herein may be used with other forms or types of implants or even without implants if only delivery of graft material to a surgical site is desired. After injection, the assembly 20 may be withdrawn, and the loading and injection procedure repeated until sufficient graft material has been delivered to the surgical site.

Figure 11:
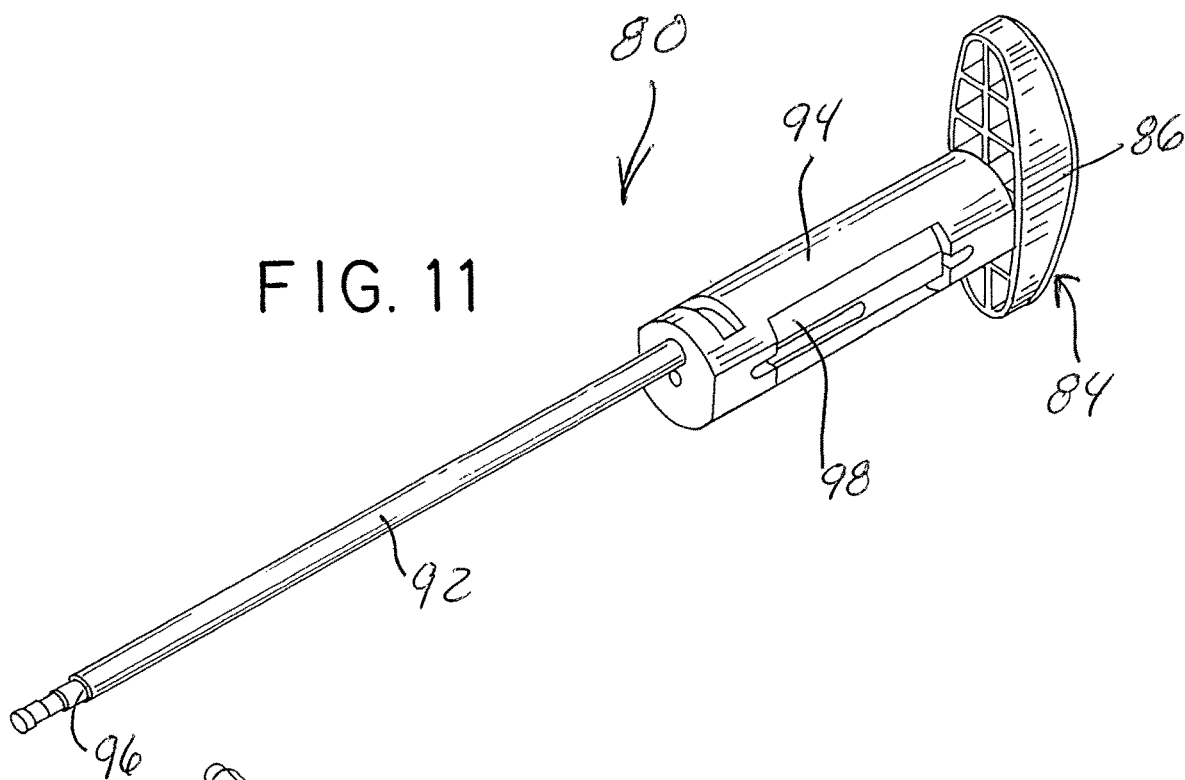
FIG. 11 is a perspective view of another embodiment of a graft material injector device/system.

An alternative embodiment of the fusion graft injection assembly or device is shown in FIGS. 11-15, and generally identified by reference numeral 80 in FIG. 11. As illustrated, the assembly or device 80 includes an injector tube and handle assembly 82 and pusher 84. The pusher 84 is constructed essentially the same as the pusher 26 described earlier, and includes a handle 86 and pusher rod 88, illustrated with a slightly enlarged blunt distal end 90.

The injector tube and handle assembly 82 includes elongated injector tube 92 and a handle or frame 94. In this embodiment the injector tube 92 includes an internal lumen that extends between the handle 94 at the proximal end and a distal end opening 96. The handle 94 has a side loading aperture 98 that is sized to receive a magazine 100 having a plurality of graft material chambers 102.

In the illustrated embodiment, the magazine 100 is illustrated in the form of a rotary cylinder with six graft material chambers disposed around the cylinder and extending through the length of the cylinder so as to be open at each end or through chambers. The cylinder is rotatable within the handle 94 to allow each of the graft material chambers to axially align with the axis of the injector tube lumen in an injection position. The proximal end of the handle 94, as in the prior embodiment, has a proximal opening 104 that is also axially aligned with the injector tube lumen, for receiving the pusher rod 88.

In this arrangement the graft material chambers 102 may be pre-filled with graft material and loaded into the handle 94 side loading opening 98. Rotation of the magazine or cylinder brings one of the chambers into axial alignment with the injector tube lumen, allowing the pusher rod 88 to be advanced through the handle proximal end opening 104, through the aligned graft chamber 102 and through the injector tube 92. In this manner, graft material in the aligned chamber can be pushed by the force of the pusher rod out of the chamber and along the injector tube lumen, exiting from the distal end opening 96 of the injector tube into the desired location at the surgical site. The pusher rod may then be retracted proximal to the magazine 100, which can be rotated to align another graft material chamber with the injector tube lumen and the pusher rod again advanced to push another quantity or bolus of graft material along the injector tube for delivery to the surgical site. This can be repeated as needed to deliver the desired amount of graft material without the need to withdraw the injector tube from the surgical site to refill it.

Although the graft material magazine is illustrated as a cylinder, it may be of any other suitable shape, such as a linear feed arrangement where the graft material chambers are disposed in a side by side relationship for sequential positioning into an aligned injection position or one behind another, if so desired. Also, the magazine may be removable from the handle to allow an emptied magazine to be refilled with graft material or replaced with a full magazine without the need to withdraw the injector tube from the surgical site.

Referring back to the figures, FIG. 11, shows the injection assembly with the magazine 100 received within the handle side loading aperture 98 and the pusher rod 88 advanced fully through the handle, the aligned graft material chamber and the injector tube lumen. The distal end 90 of the pusher rod may be seen extending beyond the distal end of the injector tube, where it may be used to tamp the graft material at the surgical site.

Figure 12:
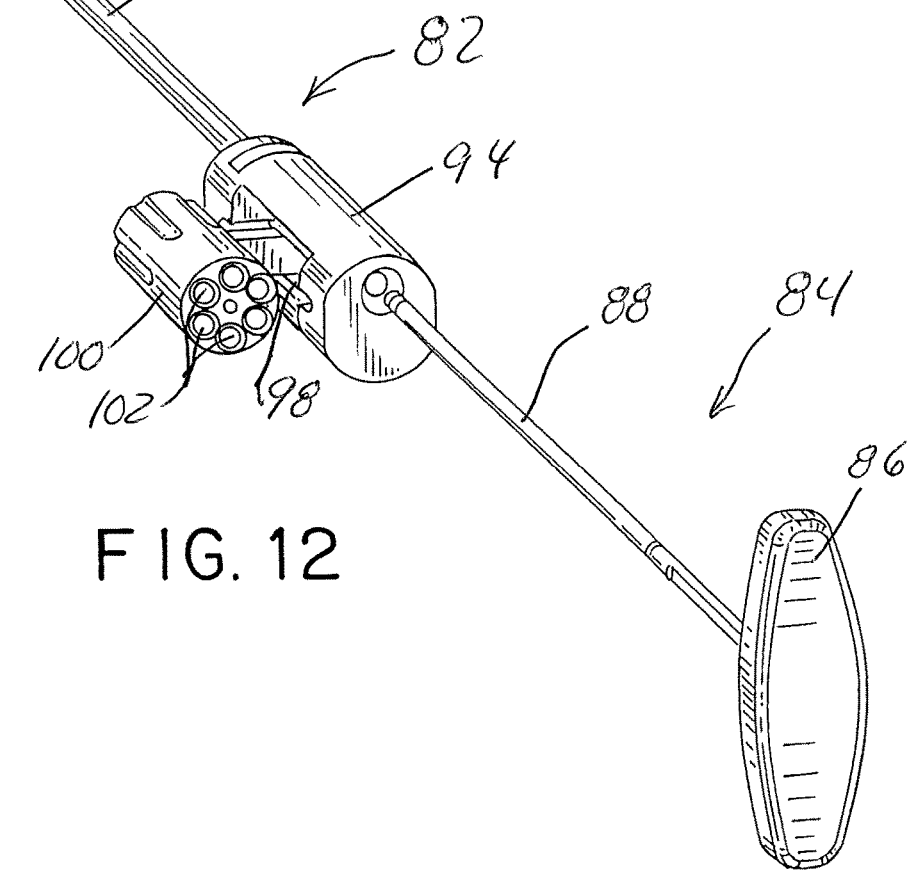
FIG. 12 is a perspective of the graft material injector device of FIG. 11 with components in different operative positions.

FIG. 12 shows the assembly 80 in a loading position with the pusher retracted to a position where the pusher rod 88 is proximal of the side loading aperture 98. This permits the magazine 100 to be inserted into the side loading aperture 98 without interference from the pusher rod 88.

Figure 15:
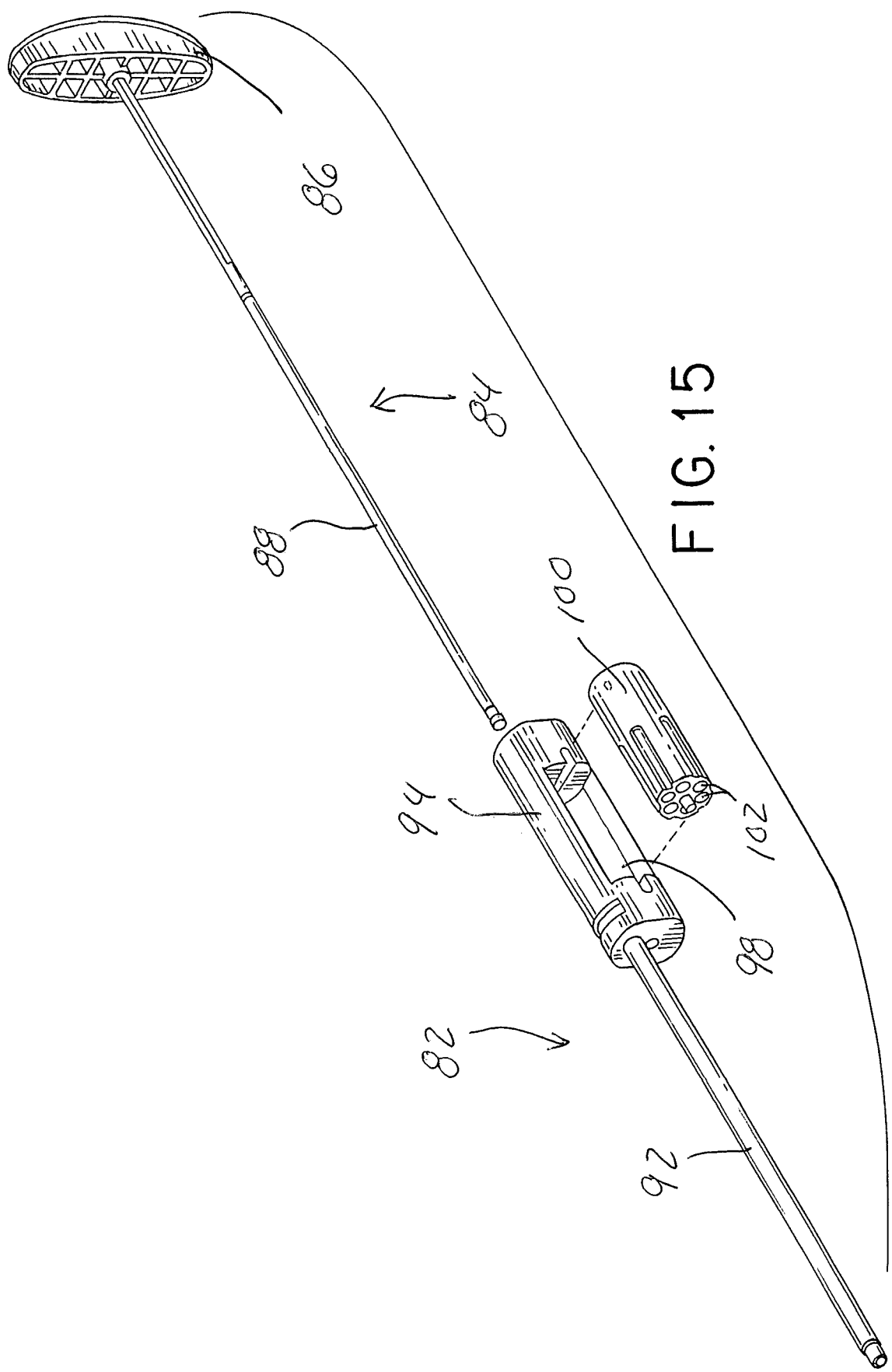
FIG. 15 is a perspective of the graft material injection device of FIG. 11 with components in different operative positions.

FIG. 13 shows a position where the magazine 100 has been inserted in the side loading aperture 98 and the pusher is positioned for insertion into proximal opening 104 in handle 94. FIG. 14 illustrates the pusher fully advanced through the handle, magazine and injector tube and extending beyond the distal end opening 96 of the injector tube. FIG. 15 illustrates a more fully exploded view of the injector assembly 80, with the magazine 100 completely removed from the side loading aperture 98.

Although the present disclosure is described in light of the illustrated embodiments, it is understood that this for the purposes illustration and not limitation. Other applications, modifications or use of the support or distraction device may be made without departing for the scope of this invention, as set forth in the claims now or hereafter filed.

The invention claimed is:

1. A graft material injector device comprising:
    an elongated injector tube comprising an internal lumen, wherein a distal end of the elongated injector tube is configured to be positioned at a surgical site;
    a magazine of graft material chambers, wherein graft material chambers of the magazine of graft material chambers are disposed in a side by side relationship; and
    a pusher rod configured to be advanced through an axially aligned graft material chamber of the magazine of graft material chambers and through the internal lumen of the elongated injector tube.

2. The graft material injector device of claim 1, further comprising a frame.

3. The graft material injector device of claim 2, wherein the magazine of graft material chambers is removable from the frame to allow an emptied magazine of graft material chambers to be refilled with graft material or replaced with a full magazine of graft material chambers without withdrawing the elongated injector tube from the surgical site.

4. The graft material injector device of claim 2, wherein the frame comprises an opening axially aligned with the internal lumen of the elongated injector tube, wherein the pusher rod is configured to be advanced through the opening.

5. The graft material injector device of claim 2, wherein the frame comprises a side loading aperture configured to receive the magazine of graft material chambers.

6. The graft material injector device of claim 1, wherein movement of the magazine of graft material chambers brings one of the graft material chambers of the magazine of graft material chambers into axial alignment with the internal lumen of the elongated injector tube.

7. The graft material injector device of claim 1, wherein the pusher rod is configured to push graft material from the axially aligned graft material chamber of the magazine of graft material chambers and along the internal lumen of the elongated injector tube.

8. The graft material injector device of claim 1, wherein the pusher rod is configured to be retracted proximal to the magazine of graft material chambers.

9. The graft material injector device of claim 1, wherein the magazine of graft material chambers is configured to be advanced to axially align another graft material chamber of the magazine of graft material chambers with the internal lumen of the elongated injector tube, and wherein the pusher rod is configured to be advanced to push another quantity of graft material to the surgical site.

10. A graft material injector device comprising:
an elongated injector tube comprising an internal lumen, wherein a distal end of the elongated injector tube is configured to be positioned at a surgical site;
a magazine of graft material chambers, wherein graft material chambers of the magazine of graft material chambers are arranged for sequential positioning into axial alignment with the internal lumen of the elongated injector tube; and
a pusher rod configured to be advanced through an aligned graft material chamber of the magazine of graft material chambers and through the internal lumen of the elongated injector tube.

11. The graft material injector device of claim 10, wherein the graft material chambers of the magazine of graft material chambers are open at each end.

12. The graft material injector device of claim 10, wherein the magazine of graft material chambers is configured to be advanced without withdrawing the elongated injector tube from the surgical site.

13. The graft material injector device of claim 10, wherein the graft material chambers of the magazine of graft material chambers are pre-filled with graft material.

14. The graft material injector device of claim 10, wherein the magazine of graft material chambers is configured to be received in a side loading aperture of a frame.

15. A method of injecting graft material comprising:
employing the graft material injector device of claim 1; and
pushing graft material by the force of the pusher rod from the axially aligned graft material chamber of the magazine of graft material chambers and along the internal lumen of the elongated injector tube.

16. The method of claim 15, further comprising retracting the pusher rod proximal to the magazine of graft material chambers.

17. The method of claim 16, further comprising advancing the magazine of graft material chambers to axially align another graft material chamber of the magazine of graft material chambers with the internal lumen of the elongated injector tube, and advancing the pusher rod to push another quantity of graft material to the surgical site.

18. The method of claim 15, further comprising advancing the magazine of graft material chambers without withdrawing the elongated injector tube from the surgical site.

19. The method of claim 15, further comprising removing the magazine of graft material chambers from a frame to allow an emptied magazine of graft material chambers to be refilled with graft material or replaced with a full magazine of graft material chambers without withdrawing the elongated injector tube from the surgical site.

* * * * *